United States Patent [19]

Carmann et al.

[11] Patent Number: 5,096,695
[45] Date of Patent: Mar. 17, 1992

[54] RADIOIODINE BENZODIAZEPINES AS BRAIN IMAGING AGENTS

[75] Inventors: Heinz Carmann, Vienna, Austria; Walter Hunkeler, Magden, Switzerland

[73] Assignee: Hoffmann-LaRoche Inc., Nutley, N.J.

[21] Appl. No.: 544,100

[22] Filed: Jun. 25, 1990

Related U.S. Application Data

[63] Continuation of Ser. No. 478,029, Feb. 9, 1990, abandoned, which is a continuation of Ser. No. 358,060, May 30, 1989, abandoned, which is a continuation of Ser. No. 229,064, Aug. 5, 1988, abandoned.

[51] Int. Cl.$^5$ ............... A61K 49/02; C07D 487/00
[52] U.S. Cl. ............................ 424/1.1; 540/498
[58] Field of Search ................... 424/1.1; 540/498

[56] References Cited

U.S. PATENT DOCUMENTS

| | | | |
|---|---|---|---|
| 4,316,839 | 2/1982 | Gerecke et al. | 540/494 |
| 4,352,818 | 12/1982 | Hunkler . | |
| 4,777,169 | 10/1988 | Earley . | |
| 4,885,152 | 12/1989 | Nakatsuka et al. | 424/1.1 |

FOREIGN PATENT DOCUMENTS

| | | |
|---|---|---|
| 027214 | 4/1981 | European Pat. Off. . |
| 0059389 | 9/1982 | European Pat. Off. . |
| 300341 | 1/1989 | European Pat. Off. . |
| 313291 | 4/1989 | European Pat. Off. . |

OTHER PUBLICATIONS

Scholl, Journal of Nuclear Medicine, vol. 24, No. 5, May 1988.
Zech, International Journal of Radiation App. and Instrumentation, Part A, 39, (1988), No. 4.
Beer et al., European Nuclear Medicine Congress, Budapest, Hungary, Aug. 24-28, 1987.
Wu et al., Soc. Nucl. Medicine (USA), Washington, D.C., Jan. 22-25.
Hunkeler et al., Nature, vol. 290, Apr. 9, 1981, p. 514.
Maziere et al., Jol. Appl., Radiat. Isot., vol. 35, No. 10, p. 973, 1984.
Shinotoh et al., J. Nucl. Med., 27, No. 10, Oct. 1986.

*Primary Examiner*—John S. Maples
*Attorney, Agent, or Firm*—George M. Gould; William H. Epstein

[57] ABSTRACT

Radioiodine 5,6-dihydro-5-methyl-6-oxo-4H-imidazo[1,5-a][1,4]benzodiazepine derivatives and their use as brain imaging agents.

6 Claims, No Drawings

RADIOIODINE BENZODIAZEPINES AS BRAIN IMAGING AGENTS

This application is a continuation of application Ser. No. 478,029 filed 2/9/90 now abandoned, which in turn is a continuation of Ser. No. 358,060, filed 5/30/89 now abandoned which in turn is a continuation of Ser. No. 07/229,064 filed 8/5/88, now abandoned.

SUMMARY OF THE INVENTION

The present invention is concerned with radioiodinated benzodiazepine derivatives of the formula

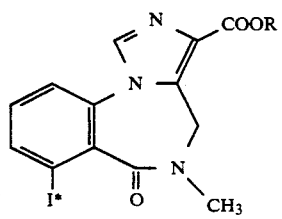

wherein I* is a radioactive iodine and R is an alkyl group with 1-4 C-atoms,
and their use in diagnosing diseases and disorders of the brain through their ability to image the brain.

DETAILED DESCRIPTION

The radioactive iodine is preferably iodine 123. The alkyl group R is preferably methyl, ethyl, isopropyl, sec.butyl or tert.butyl, most preferably ethyl.

Thus the most preferred compound according to the instant invention is ethyl-7-$^{123}$iodo-5,6-dihydro-5-methyl-6-oxo-4H-imidazo[1,5-a][1,4]benzodiazepine-3-carboxylate.

The compounds of formula I are useful for imaging the brain. As will therefore be appreciated the compounds of formula I demonstrate rapid accumulation in the brain indicative of an ability to penetrate the so-termed "blood/brain barrier". The compounds of formula I demonstrate rapid localization of the radioiodine in the brain following intravenous administration.

The compounds of formula I can be used to diagnose diseases or disorders of the brain by imaging changes in the distribution of the benzodiazepine receptors in the brain. In this manner, the compounds of formula I can be used to diagnose such brain diseases and disorders as cerebro-vascular diseases (e.g. stroks), neurological diseases (e.g. epilepsy) and psychotic diseases.

The compounds of formula I can be prepared by methods recognized in the art. For example a compound of formula I can be prepared from a cold compound of formula I, i.e. a compound, wherein I is a stable iodine, by exchange with a radioactive iodine, preferably iodine 123.

For the exchange radiolabeling process, iodine 123 in a 0.1N sodiumhydroxide solution is utilized. This solution is heated with a solution of the cold compound of formula A: i.e. a compound corresponding to formula I but wherein I is stable iodine and not iodine 123 for from about ¼ to about 2 hours. The exchange radiolabeling is carried out in the presence of a solvent such as, for example, glacial acetic acid.

A further and preferred method for preparing the compounds of formula I consists of reacting a compound of the formula

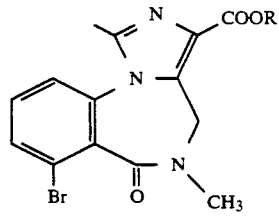

with a radioactive iodine.

Most preferably iodine 123 is used.

The same reaction conditions are used as in the case of the exchange of the non-radioactive iodine by the 123 iodine.

The cold compounds of formula I and the compounds of formula II are either known from European patent publications No. 27214 or 59389 or U.S. Pat. No. 4,316,839. These cold compounds can be prepared according to the methods given in the above European and U.S. patent publications.

As stated above, the radioiodine containing compounds of the invention rapidly localize in the brain following intravenous administration. In most instances, a sufficient amount of the administered dose will accumulate in the brain within from about two to ten minutes to permit the taking of scintiphotos. The compounds of the invention will show meaningful presence in the brain for at least 60 minutes so that significant studies may be carried out.

The radioiodinated compounds of the subject invention may be administered in an aqueous or aqueous/alcoholic medium. Such media may also contain conventional pharmaceutical adjunct materials such as, for example, pharmaceutically acceptable salts to adjust the osmotic pressure, buffers, preservatives and the like.

A preferred vehicle for the parenteral administration of the compounds of formula I is normal saline which would contain from about 0.5% by weight to about 2% by weight of a suitable preservative.

The radioactive benzodiazepine of this invention can be injected intraveneously into a patient for diagnostic imaging of the brain. In accordance with this invention, the radioactive benzodiazepine of formula I is administered in a single unit injectable dose. Any of the common carriers, such as sterile saline solution, plasma, etc. can be used for preparing the injectable solution for use to diagnostically image in accordance with this invention. Generally, the unit dose to be administered contains radioactivity of about 2 mCi to about 10 mCi, preferably about 4 to 5 mCi. However, any amount of the compound which is effective for imaging the brain can be injected in accordance with this invention. The solution to be injected is preferably in a unit dosage form of about from 0.1 milliliters to about 10 milliliters preferably from about 1 to 5 milliliters and more preferable 4 to 5 milliliters. After intravenous administration, the radioactive benzodiazepine of formula I will image the organs in vivo. Any conventional method of visualizing or imaging for diagnostic purposes can be utilized in accordance with this invention. In this respect scintiscanning means can be used to visualize or image the brain.

In accordance with this invention, the compound of formula I and particularly ethyl-7-$^{123}$iodo-5,6-dihydro-5-methyl-6-oxo-4H-imidazo[1,5-a][1,4]benzodiazepine-3-carboxylate is administered to humans intraveneously in a normal saline solution containing 5% glucose. The dose injected into humans contained 4 to 5 mCi of this radioactive compound. Within 40-60 minutes after injection, scintiphotos were made during 25 minutes with a Gamma Spect. camera. In accordance with a preferred enbodiment this compound is injected at a dose of 0.054 mCi per kg.

The compound of formula I can be administered as a free base or as a pharmaceutically acceptable acid addition salt.

The following examples further illustrate the invention. Unless otherwise noted, all temperatures are in degrees centigrade.

EXAMPLE 1

The labelling procedure for halogen exchange (bromide-iodide) was performed in a conical reaction vial tightly closed by a teflon laminated silicon septum. I-123 activity (up to 300 mCi) in 0.1n NaOH was evaporated to dryness by means of a gentle stream of nitrogen at 90°. Then 1 mg of ethyl-7-bromo-5,6-dihydro-5-methyl-6-oxo-4H-imidazo [1,5-a][1,4]benzodiazepine-carboxylate dissolved in 200 $\mu$l glacial acetic acid was added and the reaction mixture heated for 1 h at 150°. After cooling this mixture was dissolved in 5 ml water and purified by HPLC. The HPLC conditions were as follows: RP-18 column (8×250) Knauer Lichrosorb 10 $\mu$m, MeOH/H$_2$O 45/55, 2 ml/min. iodide: k'=0.0, bromo-derivate: k'=2.75, iodo-derivate: k'=4.00. The purification was performed on a device consisting of a valco 6-port valve with 20 ml loop, a Waters 510 pump, a Kontron 740 LC detector and a NaI scintillation detector. Labelling and purification was done in a lead box which was equipped for remote control handling. The labelling was virtually quantitative.

EXAMPLE 2

During the HPLC-separation the product peak was collected and afterwards evaporated to dryness with a Rota-Vapor. The residue was dissolved in a solution containing 5% glucose and passed through a silver powder column to adsorb iodine liberated during the Rota-Vapor treatment. After sterile filtration and adjustment of the activity concentration to 1 mCi/ml the ethyl-7-$^{123}$iodo-5,6-dihydro-5-methyl-6-oxo-4H-imidazo[1,5-a][1,4]benzodiazepine-carboxylate was ready for use.

The product quality was monitored with thin layer chromatography on silica gel, developed with ethylacetate/NH OH 200/1.

EXAMPLE 3

The starting material used in Example 1 was prepared as follows:

To a mixture of 167.95 g (624 mmol) of 6-bromo-3,4-dihydro-4-methyl-2H-1,4-benzodiazepine-2,5(1H)-dione, 600 ml of N,N-dimethyl-p-toluidine and 800 ml of chloroform are added dropwise at the boiling temperature of the mixture 160.8 g (1,05 mol) phosphorus oxychloride whereupon the reaction mixture is boiled under reflux for 4 hours. The resulting solution is poured on a cold mixture of 500 g sodium bicarbonate and 2 l of water and stirred during 40 minutes. The anorganic phase is separated and extracted three times with chloroform. The combined organic layers are dried over magnesium sulfate and the chloroform is removed under reduced pressure.

In the meantime a solution of 76 g (677 mmol) potassium-t-butylate in 200 ml of dimethylformamide is cooled to $-45°$, whereupon first 71 g (625 mmol) isocyanoacetic acid ethylester are added and then at $-50°$ to $-20°$ the above mentioned solution of the iminechloride is added dropwise. After removing of the cooling means the reaction mixture is stirred during 1.5 hours, whereupon 13 ml acetic acid are added and then the reaction mixture is poured on to 1800 ml of water and extracted five times with each 500 ml methylene chloride. The combined organic extracts are washed three times with water, dried over magnesium sulfate and evaporated. The raw product is recrystalized from methylene chloride and ethyl acetate and yields 156.80 g of ethyl 7-bromo-5,6-dihydro-5-methyl-6-oxo-4H-imidazo[1,5-a][1,4]-benzodiazepine-3-carboxylate of melting point 214°-215°.

EXAMPLE 4

Iodide-iodide exchange labelling was performed exactly as described for bromide-iodide exchange, but ethyl-7-iodo-5,6-dihydro-5-methyl-6-oxo-4H-imidazo[1,5-a][1,4]benzodiazepine-3-carboxylate was used as precursor. This labelling was performed to assure the identity of the labelled product in HPLC and thin layer chromatography.

EXAMPLE 5

The starting material used in Example 4 was prepared as follows:

To a mixture of 185.5 g (558.8 mmol) of 3,4-dihydro-5-iodo-4-methyl-2H-1,4-benzodiazepine-2,5(1H)-dione, 70 ml of N,N-dimethyl-p-toluidine and 800 ml of chloroform are added dropwise at the boiling temperature of the mixture 91.6 ml (979 mmol) phosphorus oxychloride whereupon the reaction mixture is boiled under reflux for 2 hours. The resulting solution is poured on a cold mixture of 490 g sodium bicarbonate and 2 l of water and stirred during 40 minutes. The anorganic phase is separated and extracted three times with chloroform. The combined organic layers are dried over magnesium sulfate and the chloroform is removed under reduced pressure.

In the meantime a solution of 75.5 g (626.6 mmol) potassium-t-butylate in 500 ml of dimethylformamide is cooled to $-50°$, whereupon first 65.2 ml (585.8 mmol) isocyano acetic acid ethylester are added and then at $-50°$ to $-15°$ the above mentioned solution of the iminechloride is added dropwise. After removing of the cooling means the reaction mixture is stirred during 1 hour, whereupon 120 ml acetic acid are added and then the reaction mixture is poured on to 1900 ml of water and extracted five times with methylene chloride. The combined organic extracts are washed three times with water, dried over magnesium sulfate and evaporated. The raw product is chromatographed on silica gel and yields after recrystallization from ethyl acetate 96.02 g of ethyl 5,6-dihydro-7-iodo-5-methyl-6-oxo-4H-imidazo[1,5-a][1,4]-benzodiazepine-3-carboxylate of melting point 244°-246°.

EXAMPLE 6

3 rats (female, Wistar, spf) are measured at 7 different points of time (2', 10', 20', 40', 1 h, 6 h, 15 h). The weight of the animals was between 113-144 g. The feeding was effected ad libitum. The i.v. injected doses varied between 184 and 355 $\mu$Ci in each 0,2 ml at injection solution.

| Percentage of the injected activity per gram of the corresponding organ (rat) | | | | | | | |
| --- | --- | --- | --- | --- | --- | --- | --- |
| | 2' | 10' | 20' | 40' | 60' | 6 h | 15 h |
| blood | 0.70 | 0.87 | 0.46 | 0.17 | 0.11 | 0.04 | 0.013 |
| brain | 2.12 | 3.22 | 2.99 | 2.70 | 1.80 | 0.05 | 0.001 |
| thyroid gland | 0.60 | 0.54 | 1.22 | 0.08 | 0.06 | 0.03 | 0.007 |
| liver | 2.38 | 5.66 | 2.62 | 0.58 | 0.19 | 0.02 | 0.016 |
| spleen | 0.60 | 0.53 | 0.29 | 0.14 | 0.07 | 0.02 | 0.010 |
| kidneys | 2.68 | 7.06 | 5.26 | 1.35 | 0.68 | 0.03 | 0.010 |
| stomach | 0.19 | 0.41 | 0.35 | 0.27 | 0.48 | 0.73 | 0.080 |
| bowel | 0.75 | 1.10 | 1.73 | 2.02 | 1.97 | 1.53 | 0.143 |
| lungs | 1.22 | 0.87 | 0.44 | 0.15 | 0.10 | 0.03 | 0.011 |
| heart | 0.86 | 0.66 | 0.30 | 0.10 | 0.06 | 0.02 | 0.007 |
| ovary | 0.88 | 0.73 | 0.53 | 0.22 | 0.16 | 0.03 | 0.011 |
| thigh bone | 0.54 | 0.45 | 0.24 | 0.10 | 0.07 | 0.02 | 0.007 |
| bladder | 0.59 | 1.07 | 0.69 | 0.24 | 0.42 | 0.57 | 0.023 |
| muscle | 0.68 | 0.42 | 0.20 | 0.09 | 0.04 | 0.01 | 0.003 |

| Percentage of the injected activity in the corresponding organs (rat) | | | | | | | |
| --- | --- | --- | --- | --- | --- | --- | --- |
| | 2' | 10' | 20' | 40' | 60' | 6 h | 15 h |
| brain | 3.11 | 5.38 | 4.20 | 4.02 | 2.42 | 0.08 | 0.0015 |
| thyroid gland | 0.18 | 0.15 | 0.18 | 0.03 | 0.02 | 0.008 | 0.0015 |
| liver | 16.90 | 34.37 | 17.61 | 3.90 | 1.29 | 0.15 | 0.107 |
| spleen | 0.26 | 0.21 | 0.11 | 0.06 | 0.03 | 0.008 | 0.0035 |
| kidneys | 3.15 | 7.48 | 6.25 | 1.53 | 0.79 | 0.04 | 0.009 |
| stomach | 0.81 | 1.20 | 1.28 | 1.37 | 1.96 | 1.35 | 0.346 |
| bowel | 9.28 | 12.70 | 22.53 | 25.54 | 28.48 | 19.50 | 1.012 |
| lung | 1.04 | 0.81 | 0.40 | 0.15 | 0.09 | 0.03 | 0.0095 |
| heart | 0.58 | 0.37 | 0.17 | 0.06 | 0.03 | 0.009 | 0.0035 |
| ovary | 0.09 | 0.06 | 0.05 | 0.02 | 0.02 | 0.003 | 0.0008 |
| thigh bone | 0.39 | 0.25 | 0.14 | 0.06 | 0.04 | 0.01 | 0.004 |
| bladder | 0.03 | 0.06 | 0.03 | 0.01 | 0.03 | 0.09 | 0.0022 |
| rest body | 63.94 | 29.92 | 25.92 | 11.04 | 7.98 | 2.88 | 1.30 |
| total body | 99.75 | 92.96 | 78.87 | 47.80 | 43.17 | 24.16 | 2.80 |
| faeces and urine | 0.05 | 6.17 | 19.39 | 48.72 | 51.71 | 48.81 | 42.69 |

We claim:

1. A radioiodinated benzodiazepine derivative of the formula

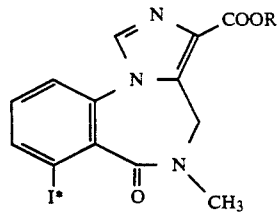

wherein R is a lower alkyl group with 1–4 C-atoms and I* is a radioactive iodine.

2. A compound of claim 1, wherein the radioactive iodine is iodine 123.

3. The compound of claim 1, wherein the said compound is Ethyl-7-$^{123}$iodo-5,6-dihydro-5-methyl-6-oxo-4H-imidazo[1,5-a][1,4]benzodiazepine-3-carboxylate.

4. A method of imaging the brain comprising injecting an effective amount of a compound of the formula:

wherein I* is a radioactive iodine and R is an alkyl group with 1–4 carbon atoms;
in a carrier suitable for injection and scanning the brain with a scintiscanning means.

5. The method of claim 4 wherein said compound is ethyl-7-$^{123}$-iodo-5,6-dihydro-5-methyl-6-oxo-imidazo[1,5-a][1,4]benzodiazepine-3-carboxylate.

6. The method of claim 4 wherein said compound is administered as a unit dose of from about Z to about 10 mCi.

* * * * *